(12) United States Patent
Gulliksen et al.

(10) Patent No.: US 6,267,748 B1
(45) Date of Patent: Jul. 31, 2001

(54) NEEDLE-RETRACTING NEEDLE HOLDER AND SYRINGE

(75) Inventors: Morten Gulliksen; Helge Kristiansen, both of Oslo (NO)

(73) Assignee: Syringus AB, Lysaker (NO)

(*) Notice: Subject to any disclaimer, the term of this patent is extended or adjusted under 35 U.S.C. 154(b) by 0 days.

(21) Appl. No.: 09/341,436

(22) PCT Filed: Dec. 12, 1997

(86) PCT No.: PCT/NO97/00338

§ 371 Date: Aug. 23, 1999

§ 102(e) Date: Aug. 23, 1999

(87) PCT Pub. No.: WO98/30261

PCT Pub. Date: Jul. 16, 1998

(30) Foreign Application Priority Data

Jan. 9, 1997 (NO) ................................ 970097
Jan. 19, 1997 (NO) ................................ 975315

(51) Int. Cl.⁷ ............................................. A61M 5/00
(52) U.S. Cl. ....................... 604/110; 604/195; 604/128
(58) Field of Search .......................... 604/110, 111, 604/187, 194, 195–198, 263, 218, 138

(56) References Cited

U.S. PATENT DOCUMENTS

| 5,049,133 | 9/1991 | Villen Pascual . |
| 5,122,118 | * 6/1992 | Haber et al. ................ 604/110 |
| 5,188,614 | 2/1993 | Hart . |
| 5,411,487 | 5/1995 | Castagna . |

FOREIGN PATENT DOCUMENTS

| 156 414 | 8/1989 | (DK) . |
| 0 479 217 | 4/1992 | (EP) . |
| 2687320 | * 8/1993 | (FR) . |
| WO 89/00435 | 1/1989 | (WO) . |
| WO 92/05818 | 4/1992 | (WO) . |

* cited by examiner

Primary Examiner—Anhtuan T. Nguyen
Assistant Examiner—Jeremy Thissell
(74) Attorney, Agent, or Firm—Young & Thompson

(57) ABSTRACT

The invention relates to a needle bolder, for use in combination with a syringe and a needle, characterized in that the needle holder is provided with an expandable element and with retention means for the expandable element, so that contact of the expandable element with an injection causes expansion of the expandable element and, as a consequence retraction of the needle into the needle holder. The invention relates too to a syringe comprising said needle holder.

25 Claims, 4 Drawing Sheets

NEEDLE-RETRACTING NEEDLE HOLDER AND SYRINGE

Figure 1:
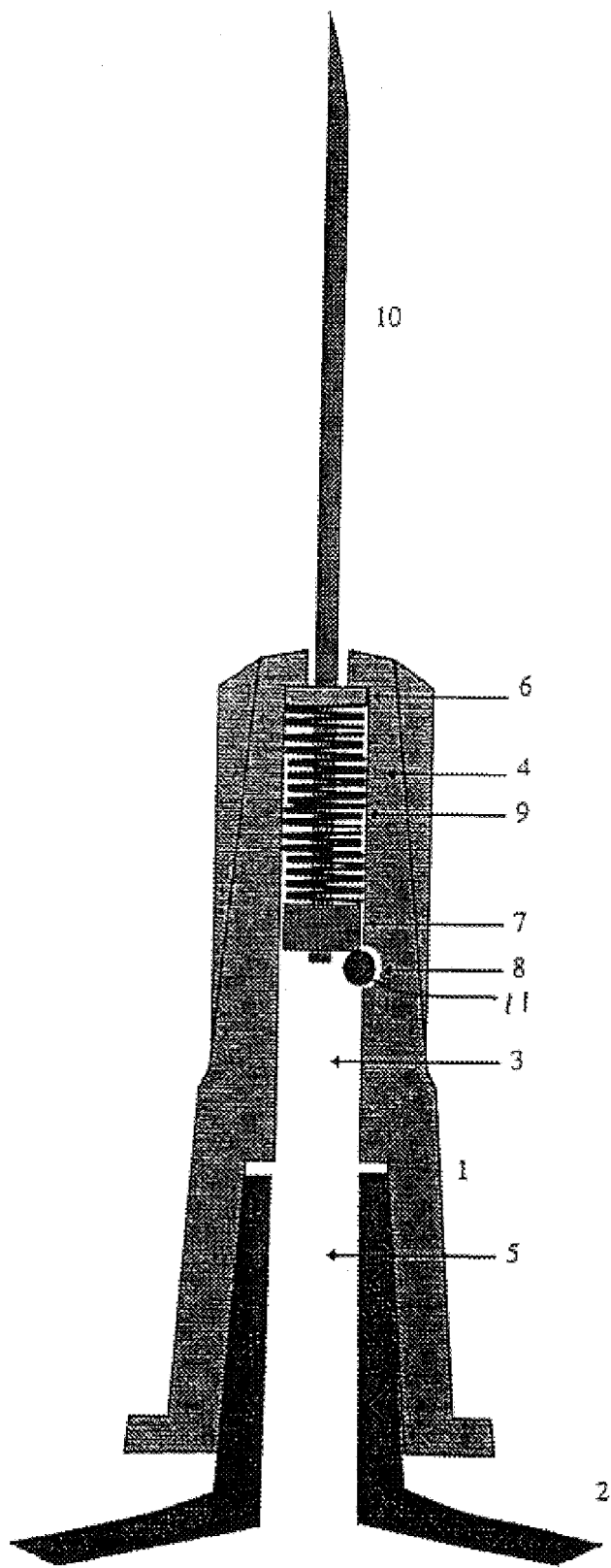

The present invention relates to an automatic needle-retracting needle-holder and syringe.

After use, syringes can be dangerous for several reasons. There is a risk of getting hurt by the needle itself, and there is a risk of contagion of serious diseases as AIDS. For this reason the need of preventing re-use of syringes is widely recognized.

There are several types single-use syringes in the market nowadays. And there are numerous known implementations of such syringes.

U.S. Pat. No. 5,122,118 shows an automatic needle retracting syringe that includes a barrel having a needle end, a plunger end, a bore, and a plunger at the plunger end. A needle gasket is slidably mounted within the bore to define a near region and a far region. A hollow needle is mounted to the needle gasket. A path through the needle gasket connects the near region to the needle. A coil spring biases the needle gasket from an extended position to a retracted position, the needle fully housed within the barrel at the latter. The extended position is maintained by a retaining capsule wedged between a narrowed bore portion and the needle gasket. This retaining gasket is a gelatin that weakens upon contact with the liquid injectant so that after the liquid injectant contacts the retaining capsule for a period of time, the spring breaks the capsule causing the needle gasket to be moved back to the retracted position, thus retracting the needle back into the barrel.

This device implies use of a gelatin that will dissolve or lose strength upon contact with the injection. A relatively high amount of gelatin is needed to form a channel capsule for housing the needle, and this and the characteristics of the material make it difficult to guarantee that it will work. Use of gelatin makes production critical and difficult. The device has one lower part that has to be placed inside the barrel, this makes it impossible to use the device together with a standard syringe, where the barrel's cross section is reduced in the end facing the needle to permit fitting of a needle holder. The spring used to withdraw the needle has to be fairly strong and this raises the cost of the syringe. The device is complicated and has many different parts, this raises too the production costs. On the other side, once the needle is retracted in the syringe, it is retained in the barrel zone, and the plunger is thus at least in part pressed out of the barrel. This is not satisfactory because it is possible to reach inside the barrel and retrieve the needle. In this case, the aim of the device is not reached. Besides, it requires high precision under production, among others to secure that the space between the barrel and the plunger is sealed. This sealing will, on the other hand, lead to humidity problems when the water does not manage to get into the sealed side channels.

U.S. Pat. No. 5,049,133 shows a safety-syringe providing a needle with a hollow core having a spring coiled around the needle. The spring is capable of expanding to retract the needle into the body of the syringe. A pressure hinge is provided with a plurality of teeth-shaped triggers for retaining the needle in a position for use and for preventing the piston from moving after use.

This is again a device that cannot be used together with standard syringes available in the market. In this device one has to be sure that the teeth-shaped triggers do not move under pressure from the injection, high precision production is therefore required. The dimensions of the device make it possible to use force and to remove the piston from the plunger, thus making possible to retrieve and reuse the needle.

U.S. Pat. No. 5,188,614 shows a protective device for use with a hypodermic syringe. The protective device comprises a hollow cylindrical casino defining a forward end wall having an opening therein, a rearward open end and an angular gripping flange adjacent the rearward end. The casing is adapted to be disposed about the syringe such that the syringe is reciprocally translatable therein with the syringe needle projecting through the opening in the forward end wall of the casing and the angular gripping flange axially spaced from the syringe flange. A dual component foaming agent is disposed in the casing adjacent the forward end wall thereof which, when the components thereof are mixed together activate to form an expanding and hardening plastic foam. Upon pressing the syringe into the casing subsequent to the ejection of fluid from the syringe, the foaming agents are activated and the expanding foam forces the syringe and syringe needle rearwardly within the casing and passes about the needle and through the forward end of the casing and hardens, thereby encapsulating the used needle within the casing and foam.

The main disadvantage of this device is that it is possible to remove the casing rapidly before the foaming agent has acted and thus retrieve the needle. The device is complicated and has many details that lead to high production costs. The two component material has besides a limited storage time, this due to the limited dimensions of the device.

WO-A 9 205 813 describes a safety syringe with retractable needle. Biasing means is attached to the syringe's barrel for biasing the needle towards a hollow plunger, and means is provided for releasing the needle into the hollow plunger by applying additional forward pressure upon the plunger after the plunger is fully extended into the barrel. The plunger comprises a cutting tip generally configured as a cylindrical knife, that cuts through a retainer arid releases a spring that forces the needle into the hollow plunger.

This mechanism requires applying additional pressure upon the barrel after the injection fluid has been taken out. If a person wants to reuse the syringe, it is sufficient to refrain from pushing the plunger further, and the needle will not be released into the plunger. This known syringe does thus not assure automatic withdrawing of the needle.

The above mentioned devices are not satisfactory because they permit easy retrieval of the needle. Besides, some are not meant for use with standard syringes. This means that use of these known devices supposes replacement of all the standardized syringes in the market by new ones, leading to high marketing costs and, what is more important, difficulties and delays in making the product available for the public. A product that protects the population must be as easy available as possible. The known devices consist in general of several small parts that have to be produced and put together with high precision, this leads to high production costs and therefore high retailing prices.

It is an object of the present invention to provide a needle holder for use together with a standardized syringe and where the retraction mechanism is housed in the needle holder.

It is a further object of the present invention to provide a needle holder that accommodates a channel needle after retraction.

It is another object of the present invention to provide a syringe equipped with a needle holder and a retractable needle, where retraction of the needle happens automatically after injection of the contents.

This objects are achieved according to the invention by a needle holder and a syringe as described in the attached patent claims.

The needle holder according to the invention is provided with an expandable element and with retention means for the expandable element so that contact of the expandable element with an injection causes expansion of the expandable element and as a consequence retraction of the needle into the needle holder.

In one preferred embodiment of the invention the expandable element comprises a spring, and the retention means comprise a stopper firmly connected to the needle, releasable connected to the needle holder by means of a connecting element and whose function is to retain the spring in compression. Upon contact with the injection, the stopper will loosen from the needle holder, and the springs will expand retracting the needle inside the needle holder. In one further preferred embodiment of the invention, the connecting element is a drop of an alginate that dissolves or loses strength upon contact with an injection. In another preferred embodiment of the invention, the connecting element is a washer.

In another embodiment of the invention, the retention means comprises also a stopper firmly connected to the needle and the needle holder houses a container where at least part of the container is expandable in the radial direction and where the radially expandable part of the container is provided with retaining means for the stopper, and the container houses the expandable element. In a preferred embodiment, the container's retaining means comprise arms separated by recesses and the arms' ends opposite the needle are curved inwards in the radial direction and form fingers that retain the stopper in position. In a further preferred version of this embodiment, the expandable element is a polymer that upon contact with the injection will expand in all directions. This will cause expansion of the lower part of the container releasing the stopper and retracting the needle.

In a third preferred embodiment of the invention, the expandable element is a container firmly attached to the needle where the container's part opposite the needle comprises a chamber limited by an osmotic membrane, and the needle holder is internally formed as a cone with a cross section increasing with the distance from the needle, so that expansion of the expandable element will cause the container to slide along the cone and thus retract the needle.

The needle holder and the syringe according to the invention have low manufacturing cost. Besides, the fact that the needle is retained inside the needle holder makes is difficult to remove the needle and retrieve it. This is because while the barrel's diameter is normally approximately 5 mm, the needle holder inner diameter is normally approximately 2 mm.

The needle holder according to the invention can be integrated to a syringe or it can be produced as a separate component attached to a syringe. The latter permits use of standardized syringes.

Figure 2:
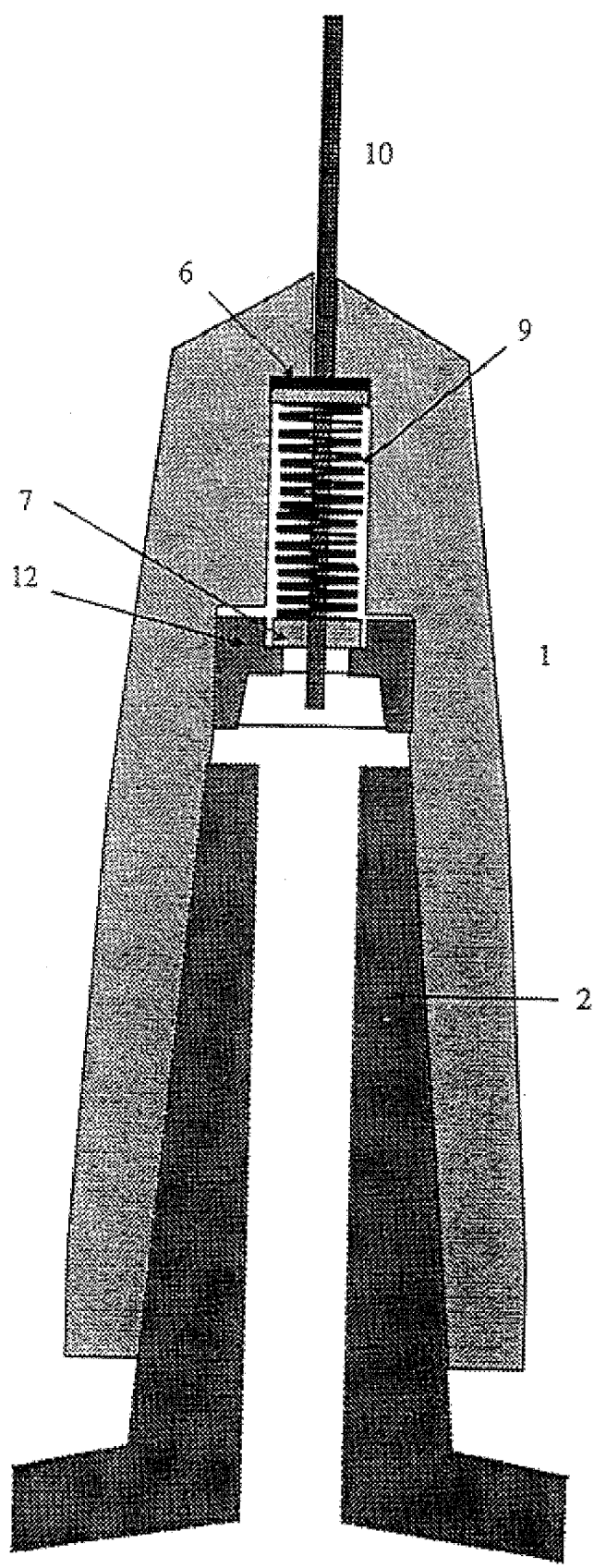
Figure 3:
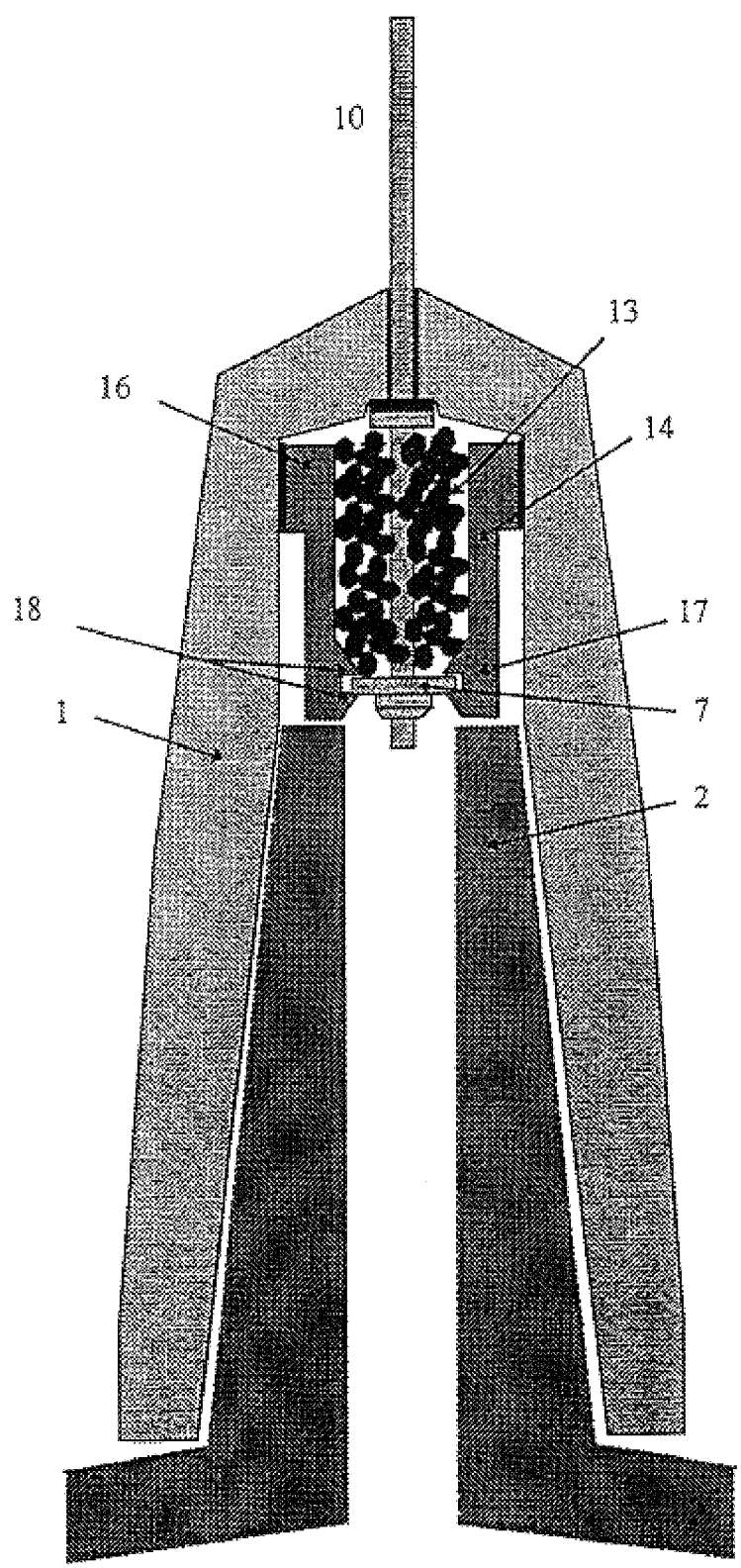
Figure 4:
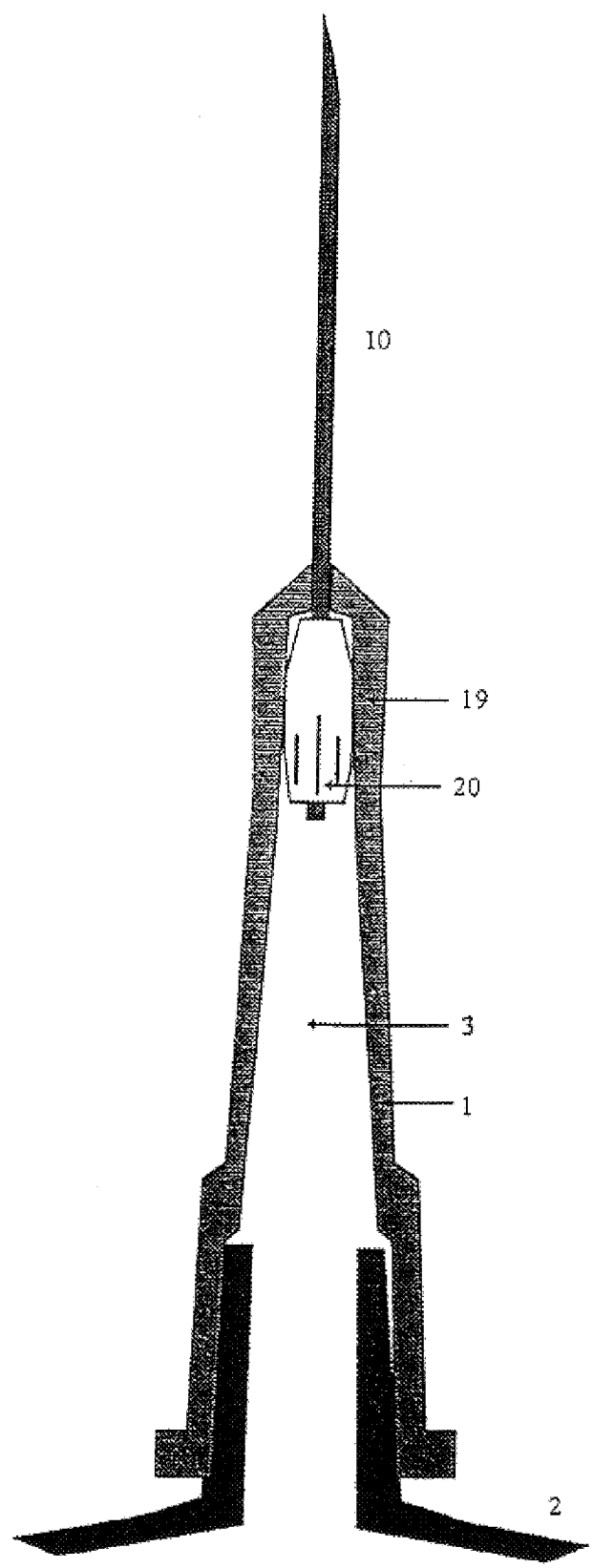

The invention will now be described by means of examples illustrated in the following drawings, where:

FIG. 1 shows a first embodiment of the invention;
FIG. 2 shows a second embodiment of the invention;
FIG. 3 shows a third embodiment of the invention; and
FIG. 4 shows a fourth embodiment of the invention.

Referring to FIG. 1, it shows a needle holder 1 according to the invention. The needle holder is fastened to the end of a syringe barrel 2 opposite the piston end. The needle holder 1 has an cylindrical axial channel 3, a needle end 4 with smaller cross-section that the cylinder end a syringe end 5 with bigger cross-section that the cylindrical channel. In the channel there is placed a first stopper 6 that abuts on the needle end 4 and a second stopper 7 that is releasably fastened to the needle holder 1 by means of a drop of alignate 8 (connecting element). Between the stoppers lies a spring 9 in compressed state. A needle 10 is firmly fastened to the second stopper 7. When the syringe is used, the injection flows in the channel 3. Upon contact with the injection, the alginate drop 8 will dissolve or at least lose it's mechanical strength. The second stopper 7 will thus be released and the spring 9 will expand. The needle 10 will retract towards channel 3 in the needle holder 1 and will be kept there by the spring 9. Several embodiments of the invention are possible in relation with the form of the alginate drop. In one embodiment of the invention, the drop is spherical. In another embodiment of the invention, it is cylindrical. In both embodiments the needle holder is provided with an opening 11 communicating with the outside, that permits fitting of the spherical or cylindrical drop in place.

FIG. 2 shows a second embodiment of the invention. In this figure the reference numbers correspond to the same parts of the needle holder and syringe shown in FIG. 1. In this embodiment, the second stopper 7 is held in place (and the spring 9 is compressed) by means of a washer 12. Said washer 12 is made of a material that upon contact with the injection will dissolve or at least lose mechanical strength. Operation of this embodiment of the invention resembles operation of the embodiment shown in FIG. 1. When the injection flows out of the syringe's barrel, the washer will dissolve or lose strength and the spring 9 will expand retracting the needle 10. In this embodiment part of the needle 10 retracts into the syringe and part of it into the needle holder 1.

FIG. 3 shows a third embodiment of the invention. In this embodiment the expandable element comprises an expandable material 13 placed inside a container 14. The container 14 comprises two parts, a >>needle end>> part 16 that is opened towards the needle holder's 1 needle end, and firmly fastened to the needle holder's 1 inner wall 16, and a >syringe end>> part that comprises arms 17 and recesses and where the arms 17 are curved inwards adjacent their free end (fingers 18) and act as retaining means for a stopper 7 firmly attached to the needle 10. When the injection flows out of the syringe's barrel and through the recesses it comes into contact with the expandable material 13, and causes said material 13 to expand. This expansion of the material 13 will separate the arms 17 and the fingers 18 will release the stopper 7. Further expansion of the material 13 will push the stopper 7 inwards and thus retract the needle 10.

FIG. 4 shows another embodiment of the invention. In this embodiment, the axial channel 3 inside the needle holder is conical, with a cross-section that increases towards the >>syringe end>>. The expandable element comprises a chamber 19 where at least part of the chamber 19 (preferably it's portion nearest the syringe end) is surrounded by an osmotic membrane 20. The chamber is firmly fastened to the needle 10. The membrane 20 will expand upon contact with the injection and will be forced inwards in the channel. The needle will thus retract.

In all the embodiments discussed here it is possible to have a needle holder that is permanently attached to the syringe and made integrally with it, or a needle holder that is attached to the syringe, eventually just before using the syringe. A needle holder integral with the syringe has the clear advantage that it is easy to use because it is not necessary to put together the pieces before using the syringe. It is also safer against tampering. On the other side, a needle holder that can be attached to the syringe, and that (as is the case with the needle holder according to the invention) is adapted for use with standardized syringes permits use of the novel needle holder with syringes that already are in the market.

The invention provides a needle holder that performs it's function in a high satisfactory way. It is easy to use for patients and practitioners. It can be produced with low costs, and therefore can have low retailing price.

For all these reasons, the needle holder according to the invention represents a clear advance in the field of medical devices.

Although the invention is described by means of special embodiments, the scope of the invention as stated in the patent claims is not to be considered in any way restricted to these embodiments.

What is claimed is:

1. Needle holder for use in combination with a syringe and a needle, comprising a spring and retention means for the spring, the retention means comprising a stopper connects to the needle and releasably connected to the needle holder, and a connecting element of alginate that releasably connected the stopper to the needle holder and that loses mechanical strength upon contact with a fluid, the spring being compressed between the stopper and the needle holder's needle end, wherein the connecting element is a drop of alginate and the needle holder is provided with at least one opening for housing said drop of alginate.

2. Needle holder according to claim 1, wherein the drop of alginate is spherical.

3. Needle holder according to claim 1, wherein the drop of alginate is cylindrical.

4. Needle holder according to claim 1, wherein the drop of alginate forms an eccentric abutment for the stopper.

5. Needle holder according to claim 1, wherein the opening for housing said drop of alginate is communicating with the outside.

6. Needle holder according to claim 1, wherein the opening permits fitting of the drop of alginate from the outside.

7. Needle holder according to claim 1, wherein the opening has an essentially semi-circular cross-section in an area adjacent to a cylindrical channel of the needle holder.

8. Needle holder according to claim 1, wherein the sum of the length of a cylindrical channel of the needle holder and the length of a needle retraction portion of the syringe barrel is essentially equal to the length of the needle.

9. Needle holder according to claim 1, wherein the sum of the length of a cylindrical channel of the needle holder and the length of a cylindrical channel of the syringe's barrel needle end is essentially equal to the length of the needle.

10. Needle holder according to claim 1, wherein the spring and the drop of alginate are disposed on opposite sides of the stopper.

11. Needle holder according to claim 1, wherein the stopper and the spring have a smaller cross section than the barrel's end facing the needle holder, so that upon expansion of the spring, the stopper and part of the spring can be placed inside said barrel's end.

12. Needle holder according to claim 1, which further comprises retention means for cooperation with retention means in said syringe.

13. Needle holder according to claim 1, which is formed integrally with said syringe.

14. Syringe comprising a barrel, a movable plunger, a needle and a needle holder according to claim 1.

15. Needle holder for use in combination with a syringe and a needle, comprising a spring and retention means for the spring, the retention means comprising a stopper connected to the needle and releasably connected to the needle holder, and a connecting element in the form of a washer that releasably connects the stopper to the needle holder and that loses mechanical strength upon contact with a fluid, the spring being compressed between the stopper and the needle holder's needle end, wherein the washer has an outer extension which is bigger than the stopper, and is provided with a central opening which is smaller than the stopper, the spring thereby forcing the stopper through the washer when the washer loses mechanical strength.

16. Needle holder according to claim 15, wherein the washer is provided with an inwardly projecting nose which defines the central opening.

17. Needle holder according to claim 15, wherein the washer is provided with an outwardly projecting portion abutting a channel of the needle holder.

18. Needle holder according to claim 15, wherein the washer is provided with an inwardly projecting nose which defines the central opening and an outwardly projecting portion abutting a channel of the needle holder, the extension of the outwardly projecting portion being much bigger than the extension of the nose in the longitudinal direction of the needle holder.

19. Needle holder according to claim 15, wherein a portion of the washer facing the stopper is provided with lateral guiding surfaces for the stopper.

20. Needle holder according to claim 15, wherein the sum of the length of a cylindrical channel of the needle holder and the length of a needle retraction portion of the syringe barrel is essentially equal to the length of the needle.

21. Needle holder according to claim 15, wherein the spring and the washer are disposed on opposite sides of the stopper.

22. Needle holder according to claim 15, wherein the stopper and the spring have a smaller cross section than the barrel's end facing the needle holder, so that upon expansion of the spring, the stopper and part of the spring can be placed inside said barrel's end.

23. Needle holder according to claim 15, which further comprises retention means for cooperation with retention means in said syringe.

24. Needle holder according to claim 15, which is formed integrally with said syringe.

25. Syringe comprising a barrel, a movable plunger, a needle and a needle holder as claimed in claim 12.

* * * * *

UNITED STATES PATENT AND TRADEMARK OFFICE
CERTIFICATE OF CORRECTION

PATENT NO. : 6,267,748 B1
DATED : July 31, 2001
INVENTOR(S) : Morten Gulliksen et al.

It is certified that error appears in the above-identified patent and that said Letters Patent is hereby corrected as shown below:

<u>Title page,</u>
Item [30], change "Jan. 19, 1997 (NO) ... 975315" to -- Nov. 19, 1997 (NO) ... 975315 --.

Signed and Sealed this

Fifth Day of March, 2002

Attest:

*Attesting Officer*

JAMES E. ROGAN
*Director of the United States Patent and Trademark Office*